United States Patent [19]

Emmons

[11] Patent Number: 5,308,243
[45] Date of Patent: May 3, 1994

[54] METHOD AND COMPOSITIONS FOR PRODUCING LIFE-LIKE DENTAL PORCELAIN RESTORATIONS AND DENTAL PORCELAIN RESTORATIONS SO PRODUCED

[75] Inventor: James D. Emmons, Rowlett, Tex.

[73] Assignee: Steven Edward Severy, Trabuco Canyon, Calif. ; a part interest

[21] Appl. No.: 946,191

[22] Filed: Sep. 17, 1992

[51] Int. Cl.⁵ .......................... A61C 13/08; A61C 5/08
[52] U.S. Cl. ................................. 433/203.1; 433/218
[58] Field of Search ........ 433/202.1, 203.1, 208.212.1, 433/218, 222.1, 223

[56] References Cited

U.S. PATENT DOCUMENTS

| | | | |
|---|---|---|---|
| 2,000,285 | 5/1935 | Hoffmann | 433/202.1 X |
| 2,377,382 | 6/1945 | Slack, Jr. | 433/203.1 X |
| 4,170,823 | 10/1979 | Smyth et al. | 433/202.1 |
| 4,189,325 | 2/1980 | Barrett et al. | 106/35 |
| 4,475,892 | 10/1984 | Faunce | 433/212.1 |
| 4,645,455 | 2/1987 | Kosmos | 433/203.1 |
| 4,828,117 | 5/1989 | Panzera et al. | 433/203.1 X |
| 4,970,032 | 11/1990 | Rotsaert | 433/203.1 X |
| 5,094,619 | 3/1992 | McLaughlin | 433/203.1 |
| 5,127,835 | 7/1992 | Yamaguchi et al. | 433/218 X |

*Primary Examiner*—Gene Mancene
*Assistant Examiner*—Nicholas D. Lucchesi
*Attorney, Agent, or Firm*—Kenneth E. Darnell

[57] ABSTRACT

The invention provides methods for making naturally appearing dental restorations, compositions of matter used in said methods and articles so formed, the resulting articles being visually life-like dental porcelain restorations formed of porcelain layers at least certain of which are modified to cause light entering a restoration to be internally reflected within the layers of the restoration to produce an opalescence virtually identical to that of natural teeth. Porcelain layers unique to the present dental restorations include colored pigments or chromas selected to replace those chromatic values which are usually absorbed within conventional porcelain restorations, the present restorations therefore transmitting essentially the same high value of light back out of the restorations which initially entered the restorations. The present restorations blend visually with adjacent natural teeth since light exiting both the restorations and the adjacent teeth enter each other and are internally reflected with similar high light values which initially entered the restorations and teeth being transmitted from said restorations and teeth to an observer.

55 Claims, 2 Drawing Sheets

METHOD AND COMPOSITIONS FOR PRODUCING LIFE-LIKE DENTAL PORCELAIN RESTORATIONS AND DENTAL PORCELAIN RESTORATIONS SO PRODUCED

BACKGROUND OF THE INVENTION

1. Field of the Invention

The invention relates generally to the production of dental porcelain restorations which are naturally appearing and relates particularly to dental restorations formed of layers of unique dental porcelains modified to internally handle light within said layers and to transmit back out of a restoration light of a value similar to the light which entered the restoration.

2. Description of the Prior Art

Dental restorations have been fabricated for centuries both for cosmetic and practical purposes. Within the last several hundred years, ceramic or porcelain powders have become the standard for forming such restorations. Reference is made to U.S. Pat. No. 3,400,097, the disclosure of which is incorporated hereinto by reference, which patent describes the use of porcelain powder by dentists and dental technicians for the build up and shaping of dental appliances such as crowns, bridges, artificial teeth and the like. These porcelain materials take the form of fine powders carried by a liquid binder which allow the formation of a "paste" such that a restoration can be built up and shaped to a desired tooth form. After shaping, the binder is typically removed such as by baking and the porcelain mass is sintered. Present conventional practice usually involves the formation of a porcelain dental restoration such as a crown or bridge on a metal framework which is called a "coping", the coping being covered conventionally by several layers of porcelain in an effort to simulate the appearance of natural teeth. A first layer of porcelain according to conventional practice is applied directly to the coping for the purpose of hiding the coping. This "opaque porcelain layer" is typically lacking any particular chromatic character. A second layer applied to the thus-coated coping is generally referred to as the "body porcelain layer" and exhibits a certain degree of translucence which is intended to be similar to that of the dentine layer of a natural tooth. Conventional practice further provides a third layer on top of the body porcelain layer, referred to as the "incisal porcelain layer", which is intended to approach the translucency of the enamel layer of a natural tooth. The various porcelain layers are typically baked between the layering steps. Pigments are typically provided in one or more of the layers referred to above to provide a color selected by a dental practitioner to be similar to that of the natural teeth or adjacent teeth or restorations present in the patient's mouth. A description of conventional restoration manufacture can be found in U.S. Pat. No. 4,828,117, the disclosure of which is incorporated hereinto by reference, this patent also providing a discussion of the formation of restorations on a ceramic base as well as on metal copings. The prior art has further provided porcelain dental restorations having fluorescing agents present in one or more porcelain layers. As an example, U.S. Pat. No. 4,645,455, the disclosure of which is incorporated hereinto by reference, describes the use of an ultraviolet fluorescing agent in the various layers of a porcelain restoration in an effort to match the appearance of a natural tooth under certain light conditions. Reference is also made to U.S. Pat. Nos. 3,880,662 and 4,645,454 which describe conventional dental porcelain powders, binders, baking and sintering processes, etc., it being understood that certain of the processes and materials described in these patents can be adapted for use according to the teachings of the present invention. For this reason, the disclosures of U.S. Pat. Nos. 3,880,662 and 4,645,454 are incorporated hereinto by reference.

Conventional practice in the art has heretofore produced somewhat less than satisfactory dental restorations. In fact, prior restorations, while adequate from the practical standpoint of use have failed to produce a warm, naturally appearing restoration which looks "life-like" or "alive". In essence, prior dental restorations including dental porcelain restorations, typically transmit gray or low value light back to an observer. The low value of light transmitted by prior dental porcelain restorations are caused in part by reflection of light off the metal surface of a coping, the light being reflected off the metal surface and going directly through the opaque layers and being thus transmitted by virtually direct reflection through the layers of the restoration. Further, prior dental porcelain restorations absorb high light values, particularly reds, yellows and oranges within the body of the restoration itself, the light being thus transmitted from the restoration being of a low value or a "gray" due to the absence of these absorbed light values. Accordingly, the present invention provides methods of making naturally appearing dental restorations, compositions of matter used in the practice of said methods and articles comprising dental porcelain restorations formed from the methods and compositions of matter, the present dental porcelain restorations being visually life-like due to the provisions of layers of dental porcelains which include pigments or chromas which cause internal handling of light in much the way light is handled internally of a natural tooth to provide an opalescent effect. Further, the present dental porcelain restorations include pigments or chromas which replace those light values, particularly the reds, yellows and oranges, which are typically absorbed by conventional dental porcelain restorations, the light thus transmitted from the present restorations being of a high value similar to light transmitted from a natural tooth. The present invention therefore provides substantial improvement in the art.

SUMMARY OF THE INVENTION

In a first aspect of the present technology, the invention provides methods for making naturally appearing dental porcelain restorations having a warm, life-like appearance. The methodology of the invention involves a layering of dental porcelain materials onto a coping or similar base member, the first layer according to the invention involving an application of a high temperature dental porcelain powder in a suitable carrier liquid and containing an appropriate chroma or colored pigment such that incident light is reflected at the proper hue. Reflection of the correct hue value by the porcelain layer covering the coping allows control of the light value so that the gray or low values of light are eliminated and high value color corrected light is reflected so that the vitality of the resulting restoration is substantially improved. A blood red pigment, such as purified selenium oxide, is added to the high temperature dental porcelain powder which is applied to the coping and the coating thus formed on the coping is fired. Optionally, chrome yellow pigment can also be added to this layer of high temperature porcelain. The resulting layer acts as a color stabilizer to reflect the correct hue value and thus to reduce gray or low value light which would otherwise be transmitted back from the interior of a dental restoration.

After application of a conventional opaque layer, a clear or translucent porcelain base layer is added, this translucent porcelain base layer including red, yellow and orange pigments with red-brown and translucent blue pigments being optional. This translucent porcelain base with pigment additives acts like a fiber optic sheet and replaces colors in the light wave which are reduced by conventional opaque layers, particularly the reds, yellows, orange colors, etc. The pigments within the opalescent, translucent porcelain layers formed according to the invention translaterally reflect and bend light entering the layers so formed, thereby to cause a spiralling by internal reflection of light within such layers. Internal reflections of the translaterally moving light occur up to 14 times, the light within the restoration being thus "handled" in a fashion similar to the way in which a natural tooth "handles" light within the tooth.

A layer of opalescent dentin according to the invention is built up between layers of the translucent porcelain base/ pigment described above, the opalescent dentin layer being shaped similarly to the pulp-dentin cavity of a natural tooth and acting as a reflective light filter. The opalescent dentin layer is a white material which thus reflects translucent white light with pigments added to the opalescent dentin layer replacing colors which are typically absorbed within a dental restoration and thus lost. The opalescent dentin is built up on the restoration at a greater thickness along portions of the interior of the restoration in order to provide a greater ability to replace colors at certain areas of the restoration so that the restoration will more closely resemble the vitality of a living tooth.

A layer of "body" porcelain is then applied, the body porcelain being a conventional material which.. can be shaded to a desired coloration. This body porcelain layer is typically referred to as the dentin layer. Optionally, yet another layer of the translucent base material can be applied over the conventional body porcelain layer.

The restoration according to a preferred embodiment of the invention can be finished conventionally with translucent incisal porcelain material and then shaped. This layer of incisal porcelain can be of varying thicknesses depending upon the thickness of the translucent base material. In some embodiments of the invention, the incisal porcelain layer can be thin relative to conventional thicknesses of incisal porcelain in conventional restorations since the present invention is desirably practiced with a layer of translucent base material immediately interiorly adjacent the incisal porcelain layer.

The invention thus provides methods for making naturally appearing dental porcelain restorations, compositions used in the present methodology and the dental porcelain restorations themselves so formed, the restorations having a warm, vital and life-like appearance due to the multiple layers of dental porcelains which are pigmented in a particular fashion to "control" or "handle" light within a resulting dental restoration such that light entering the restoration also exits the restoration with the appropriate hue values.

Accordingly, it is an object of the invention to provide methods, compositions and articles embodied as dental porcelain restorations and which have life-like warm and vital appearances.

Another object of the invention is to provide methodology for fabricating a dental porcelain restoration wherein light entering the restoration encounters colored pigments which cause the light to move translaterally of the surface of the restoration and to exit the restoration with warm hues of correct value being replaced in the exiting light.

A further object of the invention is to provide dental porcelain restorations having warm and vital life-like appearances and which can be readily produced according to methodology also a part of the invention, the resulting dental restorations blending visually with adjacent natural teeth.

Further objects and advantages of the invention will become more readily apparent in light of the following detailed description of the preferred embodiments.

DESCRIPTION OF THE PREFERRED EMBODIMENT

Figure 1:
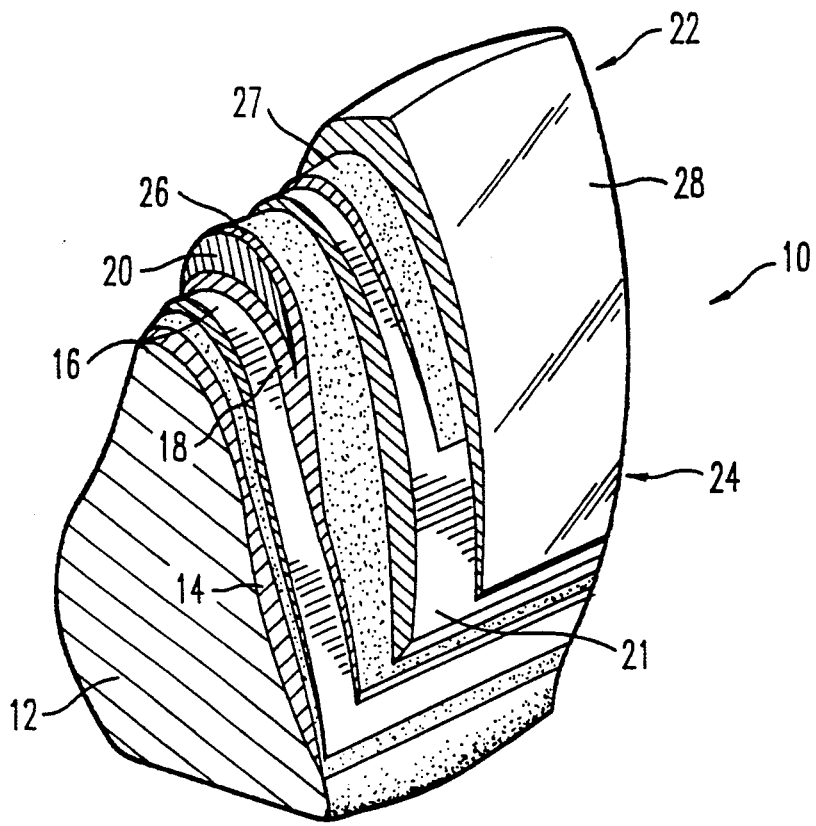
FIG. 1 is an idealized perspective view of a dental porcelain restoration according to the invention and illustrating the build-up of layers of porcelain material to form the restoration.
Figure 2:
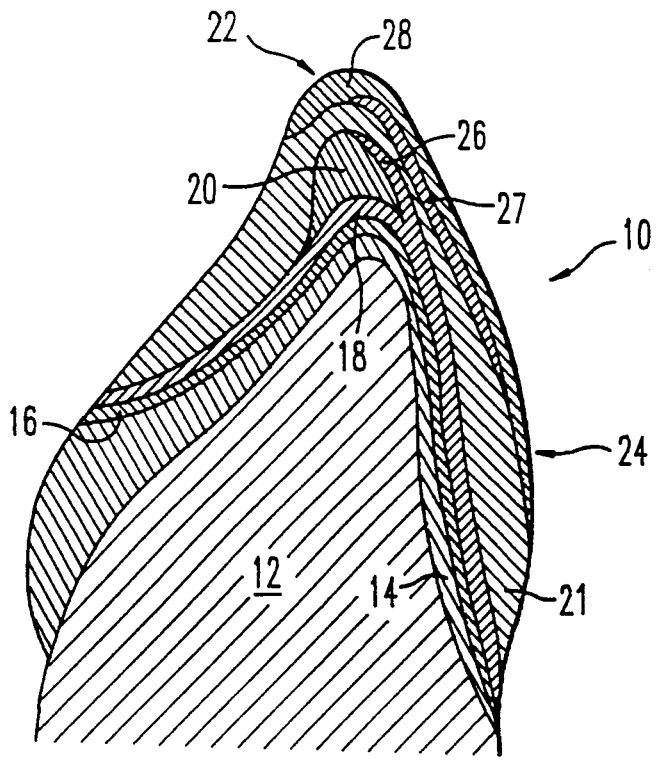
FIG. 2 is an idealized elevation in section of the dental porcelain restoration of FIG. 1; and, FIG. 3 is an idealized perspective view of a restoration according to the invention whereby modified translucent porcelain layers are formed between conventional opaque, body and incisal layers.

Referring now to the drawings and particularly to FIGS. 1 and 2, a dental restoration is seen in FIG. 1 at 10 to have portions of the various layers forming the restoration peeled away in order to illustrate the relationship of the layers which form the restoration. FIG. 2 illustrates the location and extent of the layers on the restoration 10. The restoration 10 is seen to be formed on a gray metal coping 12 as is standard in the dental laboratory. The coping 12 could be formed of other materials including ceramics. However, a metal coping is illustrated at 12 in order to best illustrate the invention and to conform with prevailing conventional practice in the industry. The coping 12, regardless of the material from which it is formed, acts to reflect light incident upon the coping essentially according to the usual "angle of incidence equals angle of reflection" physical law. For this reason, a coping such as the coping 12 reflects light back out of a dental restoration at a "low" value, that is, the light reflected by the coping 12 and transmitted back out through the restoration 10 is a gray hue and thus a low value light. For this reason, a coping such as the coping 12 typically tends to form an internal "shadow" within a conventional dental restoration and thereby reduces the vitality of the restoration.

The method of the present invention intends to control the gray reflection from a coping such as the coping 12 of a conventional restoration by controlling the reflection of light incident on the coping, thereby increasing the vitality and life-like appearance of the restoration 10 formed according to the invention. A first step as taught by a preferred embodiment of the invention is the disposition of an interface color stabilizing layer 14 over the surface of the coping 12. The stabilizing layer 14 is formed of a high temperature dental porcelain powder containing a blood red pigment or chroma and optionally a chrome yellow pigment or chroma. The porcelain powder from which the stabilizing layer 14 is formed is a conventional feldspar and silicon dioxide material containing oxides of sodium, potassium, aluminum and tin with the material being high in tin. Such a material is referred to in the industry as "white body" or "white opaque modifier" and is available from a number of dental supply companies including Ceramco of Long Island City, N.Y. The particle size of the dental porcelain powder ranges from approximately 20 to 35 microns with 30 microns being the typical powder size. This conventional porcelain powder is then modified according to the invention to include a blood red pigment which comprises a purified selenium oxide having a particle size of approximately two microns and less. The stabilizing layer 14 can include the blood red pigment in a range of 5 to 20% by weight. Optionally, a chroma yellow pigment, such as available from Semco of Zurich, Switzerland can be present in the layer 14 in a range of 0.1% to 1% by weight, the particle size of the chrome yellow pigment typically being 2 to 3 microns. The high temperature dental porcelain comprising the stabilizing layer 14 is mixed in powder form with the selenium oxide or blood red pigment and optionally the chrome yellow pigment, this mixture being held together by a carrier liquid as is conventional in the art and applied by conventional techniques to the coping 12. Typical carriers include ethyl alcohol, polyvinyl alcohol, water, etc. The stabilizing layer 14 is then fired at a temperature of 1800° F. to 1875° F. The dental porcelain powder forming the stabilizing layer 14 is chosen to be a high temperature firing material so that the stabilizing layer 14 will not be effected by subsequent firings of various porcelain layers which typically occur at lower temperatures.

The interface color stabilizing layer 14 causes a balancing of light incident on the coping 12 and layer 14, that is, light entering the restoration 10, with light which exits the restoration 10 due to reflection from the coping 12/layer 14. The stabilizing layer 14 acts to cause a reflection of higher value, that is, whiter, light which substantially adds vitality and a warm, alive appearance to the restoration 10. In essence, the chroma values introduced into the stabilizing layer 14 "replace" the wavelengths of higher value light in the exiting, reflected light which are lost by absorption within the restoration 10 as incident light penetrates the restoration 10 down to the level of the coping 12 and stabilizing layer 14.

An opaque masking layer 16 is disposed over the stabilizing layer 14, the opaque masking layer being formed of conventional materials including an opaque dental porcelain powder and suitable carrier which is sprayed or otherwise applied to the restoration 10, the assembly then being baked or fired to harden the opaque masking layer 16. The opaque masking layer 16 can be of a thickness half or less than is the practice in conventional restoration manufacture due to the presence of the stabilizing layer 14. Typically, the opaque masking layer would be formed of a thickness of approximately 2/100 of a millimeter and need not be of a greater thickness due to the presence of the stabilizing layer 14. It is to be understood that most conventional restorations utilize a layer of this "opaque" material and that this opaque material is usually applied directly to the surface of the coping 12.

A modified translucent porcelain layer 18 is then applied over the opaque masking layer 16, the layer 18 being formed according to the invention of a translucent porcelain base powder which is referred to as a 96% translucent porcelain base and which is available from American Thermacraft of New Jersey and from other manufacturers. A translucent porcelain base powder of this type includes porcelain powders having particle sizes of 65 microns, 40 microns, 20 microns, 12 microns and 6 microns, all of these particle sizes being included in varying proportions to form this conventional 96% translucent porcelain base material. This porcelain base material is modified according to the invention to include approximately 1% each of a red chroma and a yellow chroma, the yellow and red chromas being optionally present up to a weight per cent level of approximately 3%. An orange chroma is present in a weight per cent range of 0.5 to 1.5% with optional chromas being present according to the choice of the user. One optional chroma is a red-brown chroma which is typically present at a weight per cent of 0.5 and up to 1.5% by weight. Another optional chroma is a translucent blue chroma which can be present in the layer 18 within a weight per cent range of 0.1 to 0.2. The translucent porcelain base powder thus described is admixed with the respective chromas in a suitable carrier and applied conventionally over the opaque masking layer 16 which is then baked or chemically hardened to a thickness range of 0.01 mm to 0.1 mm.

The materials forming the modified translucent porcelain layer 18 are used to form one or more other layers of the restoration 10 according to certain embodiments of the invention, these materials in the finished layer 18 acting, as the materials would act in other layers not yet identified, to replace colors in the light exiting the restoration 10 which are typically reduced or lost in the various opaque and/or translucent layers of a conventional dental restoration. These colors are typically the reds, yellows, oranges, etc., which colors must be replaced in light which exits the restoration 10 in order for the restoration 10 to have a warm, vital and life-like appearance. The chroma materials present in the layer 18 not only act to replace these colors which are absorbed and not transmitted but also act to move light within the restoration 10 in a translateral sense by radically bending light waves such that light is not merely reflected out of the restoration 10 at an angle essentially identical to the angle of incidence of light into the restoration 10. In essence, the chroma materials in the layer 18 cause light to spiral away internally of the layer 18 and restoration 10 and to be internally reflected up to fourteen times prior to exit from the restoration 10. Thus, the movement of the light within the restoration 10 is controlled through the use of the chroma materials, the light thus being "moved" within the restoration 10 being a high value light which includes light of the necessary wavelengths to produce a restoration having a life-like appearance. In essence, the modified translucent porcelain layer 18 as well as other layers of the restoration 10 which can be formed of the same material as is the layer 18 acts in the manner of a fiber optic sheet to move light around within the restoration 10. The layer 18 can conveniently extend over the full surface of the layer 16 on rear portions of the restoration 10 although the layer 18 exhibits much less function on the rear of the restoration relative to the front of the restoration.

An opalescent dentin layer 20 unique to the invention is formed over at least portions of the modified translucent porcelain layer 18 and is desirably shaped into the form which a natural dentin and pulp cavity would take. Thus, the opalescent dentin layer 20 can be 4 to 5 mm at the areas of greatest thickness and 1/100 of a mm at those areas of least thickness. The areas of greatest thickness of the opalescent dentin layer 20 are at the incisal and interproximal areas of the restoration 10. The opalescent dentin layer 20 acts as a reflective light filter and uses opal chroma added high value particles to reflect white translucent light. The material forming the opalescent dentin layer 20 comprises a dental porcelain powder which can be the same dental porcelain used in forming the stabilizing layer 14 and which is known as "white body" or "white opaque modifier" and preferably is a translucent material. The chroma materials employed in the opalescent dentin layer constitute those same chroma materials used in the formation of the modified translucent porcelain layer 18 but are present in weight percentages of approximately ten times greater than is used in the layer 18. For example, an appropriate mixture of materials used to form the opalescent dentin layer 20 includes 4 parts by weight of translucent "white body", that is, translucent dental porcelain powder, 2 parts by weight of yellow pigment, 1½ parts by weight of red pigment, 0.2 parts by weight of red-brown pigment, 0.5 parts by weight of white opaque (nontranslucent) porcelain powder and 0.5% by weight of the mixture of materials forming the modified translucent porcelain layer 18. While the mixture so described provides excellent results, it is to be understood that red and yellow chromas can each constitute up to 45% of an opalescent dentin layer mixture with a range of approximately 10% to 30% being preferred for the red and yellow chromas, a range of 5 to 15% being possible for an orange chroma with optional red-brown and translucent blue being present respectively in ranges of approximately 2% to 5% and 1% to 2%. Translucent porcelain powder is preferred in the makeup of the opalescent dentin layer 20. However, the mixture can include up to 10% by weight of nontranslucent white opaque powder.

The materials forming the opalescent dentin layer 20 are mixed together and suspended in a suitable carrier for application over the layer 18. The opalescent dentin layer 20 is formed at a greater thickness in the incisal area referred to as 22 and in the interproximal regions referred to by the numeral 24. These regions correspond to the location of a natural dentin and pulp cavity in a natural tooth.

The opalescent dentin layer 20 further acts to move light translaterally within the restoration 10 and to replace colors which are typically absorbed by dental opaque around the edges of a restoration, that is, within the incisal area 22 and the interproximal regions 24 of a typical restoration. As does other layers within the restoration 10, the opalescent dentin layer 20 replaces the red, yellow and orange wavelengths which are essential to the production of a restoration having a warm and vital appearance.

The multiple functions of the opalescent dentin layer 20 include acting as a light filter and as a lightchannel surface to direct light to and from adjacent natural and/or restored teeth. The opalescent dentin layer 20 allows at least some light to filter through into the interior of the restoration and to stay in motion as the reds, yellows and oranges are reflected. In a conventional restoration, the reds, yellows and oranges are absorbed due in part to penetration of the light wave to a great depth in such conventional restorations. Accordingly, reflected light in conventional restorations is of a low value, i.e., the reflected light has a high level of perceived gray. Low value pockets of light are formed in conventional restorations at typical depths within the restorations with these low value pockets being directly adjacent to highly reflective tooth preparation surfaces. These low value pockets cause tooth forms to show through the finished conventional porcelain restoration. The light filtering/reflecting capability of the opalescent dentin layer 20 eliminates these low value pockets of light.

The opalescent dentin layer 20 can be baked after application or can be hardened such as by the use of a conventional water/acrylic plasticizer hardener liquid. At this point in the manufacture of the restoration 10, it is necessary only to cause the opalescent dentin layer 20 to stay in place throughout subsequent fabrication steps.

A second modified translucent porcelain layer 26 is then applied over at least forwardly facing surfaces of the opalescent dentin layer 20, the materials forming this layer 26 being essentially identical to the materials which form the modified translucent porcelain layer 18. After application of the layer 26 in a conventional manner, the assembly may then be baked or fired. Final layers can now be applied before firing.

In a preferred embodiment of the invention, a layer 21 of conventional "body" porcelain material is built up over at least portions of the layer 26 and over at least front portions of the layer 18. The layer 21 is typically formed over the rear portions of the layers 20 and 18 and is used to build up the restoration. The layer 21 is shaded usually according to the instructions of a dentist using known shading and matching techniques. This "body" porcelain material is produced by a number of companies including Ceramco. In a conventional restoration, the "body" porcelain forming the layer 21 would be applied directly over the opaque masking layer 16.

According to a preferred embodiment of the invention, a layer 27 formed of the same material as forms the layers 18 and 26 is applied over the layer 21. As is noted in FIG. 2, the layer 27 only needs to cover the front of the restoration 10. The layer 27 functions essentially identically to the function of the layers 18 and 26.

The restoration 10 may then be finished with a conventional incisal layer 28 which is formed of opaque dental porcelain powder in a suitable carrier, such powders being conventional in the art and generally being referred to as translucent incisal powder or enamel powder. This incisal porcelain material is applied in a conventional fashion and then baked or fired after shaping. Shaping subsequent to firing also constitutes a standard practice in the industry. The dental restoration 10 is thus completed according to a preferred embodiment of the invention. Even though major body portions of the restoration 10, such as the incisal layer 28 inter alia, act to absorb high light values, the restoration 10 maintains the high light values of a natural tooth by means of the effect of the layers 14, 18, 20, 26 and 27 which modify light exiting the restoration 10 to replace hues lost by absorption of those hues from light entering the restoration. The translateral movement of light within the restoration 10 caused by internal reflections from the chroma particles disposed within the various unconventional layers 14, 18, 20, 26 and 27 further acts to cause the restoration 10 to exhibit warmth and life-like vitality. The restoration 10 actually blends with adjacent teeth, whether natural or artificial, due to the fact that the restoration 10 "exchanges" light with the adjacent structures.

Figure 3:
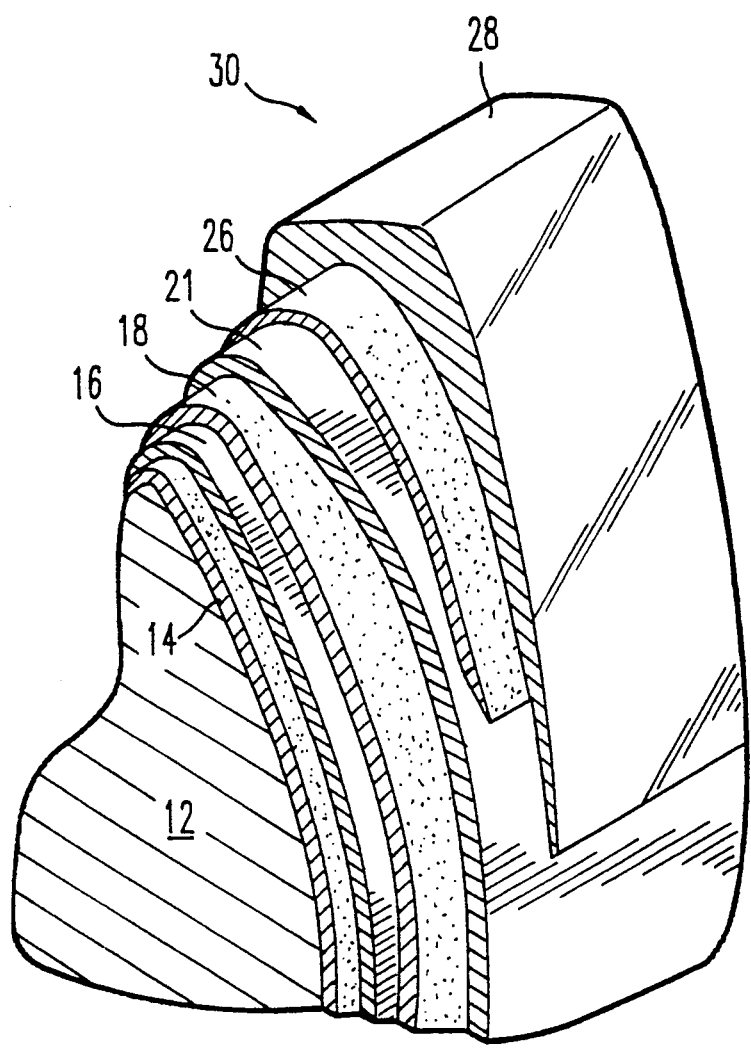

Referring now to FIG. 3, a restoration 30 is shown to be similar in structure to the restoration 10. However, layers equivalent to the layers 18 and 26 of FIG. 1 sandwich a layer of "body" opaque which is essentially identical to the layer 21 of FIG. 1. The restoration terminates in a layer essentially identical to the incisal layer 28 of FIG. 1. The several layers of FIG. 3 are numbered identically to the corresponding layers of FIG. 1 according to the similarity of materials forming the respective layers.

Of particular note is the fact that the opalescence exhibited by the present restorations cannot be burned out of the restorations by repeated firings. Prior attempts to produce a natural appearing opalescence in dental restorations have had as serious failings including the fact that the degree of opalescence exhibited by those restorations was extraordinarily susceptible to being burned out in the event that firing temperatures were not controlled or if multiple firings were necessary in a layer process. The ability of the present compositions of matter to maintain opalescence through repeated firings provides a further advantage to the use of the present methodology and compositions of matter and the resulting dental restorations.

It is to be understood that the drawings are idealized representations of the various layers of materials forming the restorations. The layers in most instances extend over the full surfaces of immediately lower layers and are shown as being cutaway short of full surface extension such as in FIGS. 1 and 3 for the purposes of illustration only. The intent of the invention is to maintain the spectral integrity or color of the light wave exiting restoration 10 so that this exiting light wave is balanced relative to the light wave entering the restoration. This balancing of the light wave spectral density is accomplished by the addition of pigmentation to the porcelain as described in detail herein. Practice of the invention thus produces the life-like opalescence referred to throughout the specification and claims.

It is to be further understood that the invention can be practiced other than as is expressly described above, the invention being limited only by the scope of the appended claims.

What is claimed is:

1. A dental restoration having a natural, warm and vital appearance, the restoration in formed on a coping and comprising layers of dental porcelain materials, the dental porcelain materials having chroma particles encapsulated therein which correct hue values of light transmitted from the restoration to replace wavelengths of light absorbed by portions of the restoration from light entering the restoration, the chroma particles further internally reflecting light within the restoration translaterally over surfaces and between surfaces of the layers forming the restoration, the coping having a color stabilizing layer of high temperature dental porcelain formed thereover, the color stabilizing porcelain layer having a red pigment comprising purified selenium oxide encapsulated therein.

2. The dental restoration of claim 1 wherein the red pigment is present in the color stabilizing layer in a weight per cent range of 5% to 20%.

3. The dental restoration of claim 1 wherein the red pigment has a particle size of approximately 2 microns.

4. The dental restoration of claim 1 wherein the color stabilizing porcelain layer has a chrome yellow pigment encapsulated therein, the chrome yellow pigment being present in a weight per cent range of 0.1% to 1.0%.

5. The dental restoration of claim 1 and further comprising a layer of opaque porcelain formed over the color stabilizing layer and a modified translucent porcelain layer formed over the opaque porcelain layer, the modified translucent porcelain layer comprising a translucent porcelain, red chroma particles, yellow chroma particles and orange chroma particles encapsulated in the translucent porcelain forming the modified translucent porcelain layer.

6. The dental restoration of claim 5 wherein the modified translucent porcelain layer further comprises red-brown chroma particles and translucent blue chroma particles.

7. The dental restoration of claim 5 wherein the red and yellow chroma particles are each present in a weight per cent range of approximately 1% to 3% and the orange chroma particles are present in a weight per cent range of approximately 0.5% to 1.5%.

8. The dental restoration of claim 7 wherein the modified translucent porcelain layer further comprises red-brown chroma particles present in a weight per cent of approximately 0.5% and translucent blue chroma particles present in a weight per cent range of approximately 0.1% to 0.2%.

9. The dental restoration of claim 5 and further comprising a layer of opalescent dentin formed over the modified translucent porcelain layer, the opalescent dentin layer comprising translucent white body porcelain and chroma particles as are present in the modified translucent porcelain layer, the chroma particles in the opalescent dentin layer being present in weight per cents approximately ten times greater than in the modified translucent porcelain layer.

10. The dental restoration of claim 9 and further comprising a second layer of modified translucent porcelain formed over the opalescent dentin layer.

11. The dental restoration of claim 10 and further comprising a layer of translucent incisal porcelain formed over the second modified translucent porcelain layer.

12. A dental restoration having a natural warm and vital appearance, the restoration being formed on a coping and comprising layers of dental porcelain materials, the dental porcelain materials having chroma particles encapsulated therein which correct hue values of light transmitted from the restoration to replace wavelengths of light absorbed by portions of the restoration from light entering the restoration, the chroma particles further internally reflecting light within the restoration translaterally over surfaces and between surfaces of the layers forming the restoration, the coping having a color stabilizing layer of high temperature dental porcelain formed thereover, the color stabilizing porcelain layer having a blood red pigment encapsulated therein.

13. The dental restoration of claim 12 wherein the blood red pigment is purified selenium oxide.

14. The dental restoration of claim 12 wherein the red pigment is presenting the color stabilizing layer in a weight percent range of 5% to 20%.

15. The dental restoration of claim 12 wherein the red pigment has a particle size of approximately 2 microns.

16. The dental restoration of claim 12 wherein the color stabilizing porcelain layer has a chrome yellow pigment encapsulated therein, the chrome yellow pigment being present in a weight percent range of 0.1% to 1.0%.

17. The dental restoration of claim 12 and further comprising a layer of opaque porcelain formed over the color stabilizing layer and a modified translucent porcelain layer formed over the opaque porcelain layer, the modified translucent porcelain layer comprising a translucent porcelain, red chroma particles yellow chroma particles and orange chroma particles encapsulated in the translucent porcelain forming the modified translucent porcelain layer.

18. The dental restoration of claim 17 wherein the modified translucent porcelain layer further comprises red-brown chroma particles and translucent blue chroma particles.

19. The dental restoration of claim 17 wherein the red and yellow chroma particles are each present in a weight percent range of approximately 1% to 3% and the orange chroma particles are present in a weight percent range of approximately 0.5% of 1.5%.

20. The dental restoration of claim 19 wherein the modified translucent porcelain layer further comprises red-brown chroma particles present in a weight percent of approximately 0.5% and translucent blue chroma particles present in a weight percent range of approximately 0.1% to 0.2%.

21. The dental restoration of claim 17 and further comprising a layer of opalescent dentin formed over the modified translucent porcelain layer, the opalescent dentin layer comprising translucent white body porcelain and chroma particles as a present in the modified translucent porcelain layer, the chroma particles in the opalescent dentin layer, the chroma particles in the opalescent dentin layer being present in weight percents approximately ten times greater tan in the modified translucent porcelain layer.

22. The dental restoration of claim 21 and further comprising a second layer of modified translucent porcelain formed over the opalescent dentin layer.

23. The dental restoration of claim 22 and further comprising a layer of translucent incisal porcelain formed over the second modified translucent porcelain layer.

24. A layer of dental restoration formed of multiple porcelain layers on a coping, comprising:
a translucent dental porcelain having encapsulated therein chroma particles including red and yellow chroma particles present in the layer i a weight percent range of approximately 10% to 30%, orange chroma particles present in a weight percent range of approximately 5% to 15%, red-brown chroma particles presenting a weight prevent of approximately 5% and translucent blue chroma particles present in a weight percent range of approximately 1% to 2%.

25. A dental restoration having a natural, warm and vital appearance, the restoration being formed on a substrate and comprising:
a color stabilizing layer of dental porcelain materials formed over the substrate; and,
means for stabilizing the color of the layer of dental porcelain materials to reflect light from the restoration which is of a value and hue of light entering the restoration and for replacing light values absorbed by the substrate and for internally reflecting light within the restoration.

26. The restoration of claim 25 wherein the color stabilizing means comprises chroma particles encapsulated within the color stabilizing layer, which chroma particles replace light values absorbed by the substrate and which internally reflect light within the restoration.

27. The restoration of claim 26 wherein the chroma particles comprise a blood red pigment.

28. The dental restoration of claim 27 wherein the red pigment is purified selenium oxide.

29. The dental restoration of claim 28 wherein the red pigment is present in the color stabilizing layer in a weight percent range of 5% to 20%.

30. The dental restoration of claim 28 wherein the red pigment has a particle size of approximately 2 microns.

31. The dental restoration of claim 27 wherein the color stabilizing layer has a chrome yellow pigment encapsulated therein.

32. The dental restoration of claim 31 wherein the chrome yellow pigment is present in a weight percent range of 0.1% to 1.0%.

33. The dental restoration of claim 26 and further comprising a layer of opaque porcelain formed over the color stabilizing layer.

34. The dental restoration of claim 33 and further comprising:
a layer of modified translucent porcelain formed over the opaque porcelain layer; and,
means formed in the modified translucent porcelain layer for translaterally reflecting and bending light entering the restoration to cause internal light reflections within the restoration and to replace colors absorbed by porcelain layers in the restoration.

35. The dental restoration of claim 34 wherein the last-mentioned means comprise red chroma particles, yellow chroma particles and orange chroma particles encapsulated in a translucent porcelain, wavelengths of light entering the restoration and which are absorbed by opaque and other porcelain layers being replaced in the light exiting the restoration by the chroma particles, the chroma particles reflecting light internally within the restoration and laterally over surfaces of the layers, thereby producing a restoration having a warm, vital and life-like appearance.

36. The dental restoration of claim 34 and further comprising:
a layer of opalescent dentin formed over the modified translucent porcelain layer, the opalescent dentin layer comprising translucent white body porcelain; and,
means formed in the opalescent dentin layer for translaterally reflecting and bending light entering the restoration to cause internal light reflections within the restoration and for replacing colors ordinarily reduced by porcelain layers to cause the light values and hues of light exiting the restoration to be equal to the light values and hues of light entering the restoration.

37. The dental restoration of claim 36 wherein the last-mentioned means comprise red chroma particles yellow chroma particles and orange chroma particles encapsulated in the opalescent dentin layer.

38. The dental restoration of claim 36 and comprising a second layer of the modified translucent porcelain formed over the opalescent dentin layer.

39. The dental restoration of claim 38 and further comprising a layer of translucent incisal porcelain formed over the second modified translucent porcelain layer.

40. A method for making a dental restoration having a natural, warm and vital appearance, the restoration being formed on a coping, comprising the steps of:

forming a color stabilizing layer of dental porcelain materials over the coping and having chroma particles encapsulated within the layer which replace light values absorbed by the coping and which internally reflect light within the restoration;

forming a layer of opaque porcelain over the color stabilizing layer;

forming a layer of modified translucent porcelain over the opaque porcelain layer, the modified translucent porcelain layer comprising a translucent porcelain, red chroma particles, yellow chroma particles and orange chroma particles encapsulated in the modified translucent porcelain layer;

forming a layer of opalescent dentin over the modified translucent porcelain layer, the opalescent dentin layer comprising translucent white body porcelain and chroma particles as are present in the modified translucent porcelain layer but at greater weight percentages;

forming a second layer of the modified translucent porcelain over the opalescent dentin; and, forming a layer of translucent incisal porcelain over the second modified translucent porcelain layer, thereby to form a dental restoration wherein wavelengths of light entering the restoration and which are absorbed by opaque and other porcelain layers are replaced by the chroma particles in the light exiting the restoration, the chroma particles reflecting light internally within the restoration and laterally over surfaces of the layers, thereby producing a restoration having a warm, vital and life-like appearance.

41. The method of claim 40 wherein the chroma particles in the color stabilizing layer comprise red purified selenium oxide particles having a particle size of approximately two microns and which are presenting the color stabilizing layer in a weight per cent range of approximately 5% to 20%; the chroma particles in the modified translucent porcelain layer being selected from the group consisting of red, yellow, orange, red-brown and translucent blue chroma particles and being present in a weight per cent range of up to 3% of the modified translucent porcelain layers; and the chroma particles in the opalescent dentin layer being selected from the group consisting of red, yellow, orange, red-brown and translucent blue chroma particles and being present in the opalescent dentin layer at weight per cent ranges greater than those ranges of said particles in the modified translucent porcelain layers.

42. The method of making a dental restoration having a natural, warm and vital appearance, the restoration being formed on a substructure such as a coping, comprising the steps of:

forming a color stabilizing layer of dental porcelain materials over the substructure and having chroma particles encapsulated within the color stabilizing layer which replace light values absorbed by the substructure nd which internally reflect light within the restoration;

forming a layer of opaque porcelain over the color stabilizing layer;

forming a layer of modified translucent porcelain over the opaque porcelain layer, the modified translucent porcelain layer comprising a translucent porcelain, red chroma particles, yellow chroma particles and orange chroma particles encapsulated in the modified translucent porcelain layer; and, forming at least one additional layer of dental porcelain over the modified translucent porcelain layer to complete the dental restoration, thereby forming a dental restoration wherein wavelengths of light entering the restoration and which are absorbed by opaque and other porcelain layers are replaced by the chroma particles in the light exiting the restoration, the chroma particles reflecting light internally within the restoration and laterally over surfaces of the layers, thereby producing a restoration having a warm, vital and life-like appearance.

43. The method of claim 42 wherein the formation of at least one additional dental porcelain layer comprises the forming of a layer of opalescent dentin over the modified translucent porcelain layer, the opalescent dentin layer comprising translucent white body porcelain and chroma particles as are presenting the modified translucent porcelain layer but at greater weight percentages.

44. The method of claim 43 wherein the step of forming at least one additional layer of dental porcelain further comprises the step of forming a second layer of the modified translucent porcelain over the opalescent dentin layer.

45. The method of claim 44 wherein the step of forming at least one additional layer of dental porcelain further comprises the step of forming a layer of translucent incisal porcelain over the second modified translucent porcelain layer.

46. The method of claim 43 wherein the chroma particles in the opalescent dentin layer are selected from the group consisting of red, yellow, orange, red-brown and translucent blue chroma particles and are present in the opalescent dentin layer at weight percent ranges greater than those range of said particles in the modified translucent porcelain layer.

47. The method of claim 43 wherein the chroma particles in the color stabilizing layer comprise red purified selenium oxide particles having a particle size of approximately 2 microns and which are present in the color stabilizing layer in a weight percent range of approximately 5% to 20%; the chroma particles in the modified translucent porcelain layer being selected from the group consisting of red, yellow, orange, red-brown and translucent blue chroma particles and being present in a weight percent range of up to 3% of the modified translucent porcelain layer; and the chroma particles in the opalescent dentin layer being selected from the group consisting of red, yellow, orange, red-brown and translucent blue chroma particles and being presenting the opalescent dentin layer at weight percent ranges greater than those ranges of said particles in the modified translucent porcelain layer.

48. The method of claim 42 wherein the chroma partials in the color stabilizing layer comprise red purified selenium oxide particles having a particle size of approximately 2 microns and which are present in the color stabilizing layer in a weight percent range of approximately 5% to 20%.

49. The method of claim 42 wherein the chroma particles in the modified translucent porcelain layer are selected from the group consisting of red, yellow, orange, red-brown and translucent blue chroma particles and being present in a weight percent range of up to 3% of the modified translucent porcelain layer.

50. A method for handling light within a dental restoration formed of dental porcelain materials disposed on a substructure to produce light values and hues exiting the restoration which re substantially equivalent to light entering the restoration, comprising the steps of:
 causing light to be directed onto and into the restoration; and,
 reflecting the light entering the restoration internally within the restoration to replace hues and light values absorbed within the substructure of the restoration from the light entering the restoration on incidence of the internally reflected light with chroma particles encapsulated within at least certain of the dental porcelain materials forming the restoration to cause light exiting the restoration to substantially include those light values and hues of the light entering the restoration.

51. The method of claim 50 wherein the light reflecting step comprises:
 forming a color stabilizing layer of dental porcelain materials over the substructure and having at least certain chroma particles encapsulated within said layer for replacing light values absorbed by the substructure and for internally reflecting light within the restoration.

52. The method of claim 51 and further comprising the steps of:
 forming a layer of opaque porcelain over the color stabilizing layer; and
 forming a layer of modified translucent porcelain over the opaque porcelain layer, the modified translucent porcelain layer comprising a translucent porcelain, red chroma particles, yellow chroma particles and orange chroma particles encapsulated in the modified translucent porcelain layer.

53. The method of claim 52 and further comprising the step of forming a layer of opalescent dentin over the modified translucent porcelain layer, the opalescent dentin layer comprising translucent white body porcelain and chroma particles as are present in the modified translucent porcelain layer but at greater weight percentages.

54. The method of claim 53 and further comprising the steps of:
 forming a second layer of the modified translucent porcelain over the opalescent dentin layer; and,
 forming a layer of translucent incisal porcelain over the second modified translucent porcelain layer, thereby forming a dental restoration wherein wavelengths of light entering the restoration and which re absorbed by opaque and other porcelain layers are replaced by the chroma particles in that light exiting the restoration, the chroma particles reflecting light internally within the restoration and laterally over surfaces of the layers, thereby producing a restoration having a warm, vital and life-like appearance.

55. The method of claim 54 wherein the chroma particles in the color stabilizing layer comprise red purified selenium oxide particles having a particle size of approximately two microns and which re present in the color stabilizing layer in a weight percentable range of approximately 5% to 20%; the chroma particles in the modified translucent porcelain layers being selected from the group consisting of red, yellow, orange, red-brown and translucent hue chroma particles and being present in a weight percent range of up to 3% of the modified translucent porcelain layer; and the chroma particles in the opalescent dentin layer being selected from the group consisting of red, yellow, orange, red-brown and translucent blue chroma particles and being presenting the opalescent dentin layer at weight percent ranges greater than those ranges of said particles in the modified translucent porcelain layers.

* * * * *